United States Patent [19]

Jäger et al.

[11] 4,360,528
[45] Nov. 23, 1982

[54] COMBATING FUNGI WITH 1-AZOLYL-1-PROPEN-3-OLS

[75] Inventors: Gerhard Jäger; Udo Kraatz, both of Leverkusen; Karl H. Büchel, Wuppertal; Paul-Ernst Frohberger, Leverkusen; Wilhelm Brandes, Leichlingen; Volker Paül, Solingen, all of Fed. Rep. of Germany

[73] Assignee: Bayer Aktiengesellschaft, Leverkusen, Fed. Rep. of Germany

[21] Appl. No.: 166,272

[22] Filed: Jul. 2, 1980

[30] Foreign Application Priority Data

Jul. 18, 1979 [DE] Fed. Rep. of Germany ....... 2928967

[51] Int. Cl.³ .............. A01N 43/50; A01N 43/64; C07D 233/60; C07D 249/08
[52] U.S. Cl. .................. 424/269; 424/245; 424/273 R; 424/232; 542/413; 542/421; 542/426; 542/429; 542/440; 542/458; 568/308
[58] Field of Search ............... 542/413, 426, 429, 458, 542/468; 424/245, 269, 232, 273 R; 548/262, 341

[56] References Cited

U.S. PATENT DOCUMENTS 3,993,765 11/1976 Buchel et al. ............... 424/269
4,005,083 1/1977 Buchel et al. ............... 424/245
4,210,656 7/1980 Zirngibl et al. .............. 542/458

FOREIGN PATENT DOCUMENTS 1795249 12/1971 Fed. Rep. of Germany ...... 548/341
2350122 4/1975 Fed. Rep. of Germany ...... 548/262
2350123 4/1975 Fed. Rep. of Germany ...... 548/341

Primary Examiner—Alton D. Rollins
Attorney, Agent, or Firm—Sprung, Horn, Kramer & Woods

[57] ABSTRACT

1-Azolyl-1-propen-3-ol of the formula

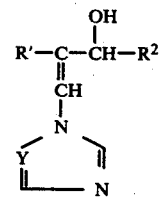

in which
  $R^1$ is an optionally substituted phenyl or phenoxy radical,
  $R^2$ is an alkyl or cycloalkyl radical, or an optionally substituted phenyl radical, and
  Y is N or CH, or physiologically acceptable acid addition salts or metal salt complexes thereof which possess fungicidal activity.

10 Claims, No Drawings

COMBATING FUNGI WITH 1-AZOLYL-1-PROPEN-3-OLS

The present invention relates to certain new azolylalkenols, to a process for their production and to their use as fungicides.

It has already been disclosed that trityl-triazoles, such as triphenyl-(1,2,4-triazol-1-yl)-methane, have a good fungicidal activity (see DE-OS (German Published No.) 1,795,249). It has also already been disclosed that 1-propyl-triazolyl or -imidazolyl derivatives, such as, in particular, 1-(imidazol-1-yl)- and -(1,2,4-triazol-1-yl)-2-phenoxy-4,4-dimethyl-pentan-3-ols which are substituted in the phenyl part, have good fungicidal properties (see DE-OS (German Published No.) 2,350,122 and DE-OS (German Published No.) 2,350,123). However, the action of these compounds is not always completely satisfactory, especially when low amounts and concentrations are applied.

The present invention now provides, as new compounds, the azolyl-alkenols of the general formula

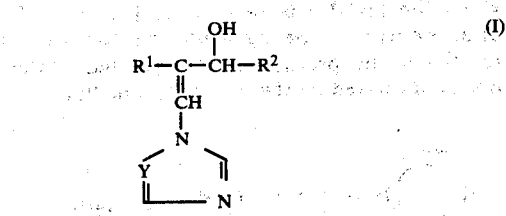

in which
$R^1$ represents an optionally substituted phenoxy radical or an optionally substituted phenyl radical,
$R^2$ represents an alkyl or cycloalkyl group or an optionally substituted phenyl radical and
Y represents a nitrogen atom or a CH group,
and physiologically acceptable acid addition salts and metal salt complexes thereof.

The compounds of the formula (I) can exist in two geometric isomer forms, depending on the arrangement of the groups which are bonded to the carbon atoms linked by the double bond. The compounds of the formula (I) have an asymmetric carbon atom and can thus also exist in the two optical isomer forms or as racemates. All the isomers and mixtures thereof are claimed according to the invention.

According to the present invention there is further provided a process for the production of azolyl-alkenol of the present invention in which an azolyl-alkenone of the general formula $$R^1-\underset{\underset{\underset{N}{\overset{|}{CH}}}{\overset{\|}{C}}}{C}-CO-R^2 \quad (II)$$

(with Y, N ring shown)

in which
$R^1$, $R^2$ and Y have the meaning indicated above, is reduced and the product is converted, if desired, into a physiologically acceptable acid addition salt or metal complex thereof.

The new azolyl-alkenones of the present invention have good fungicidal properties. Surprisingly, the compounds according to the invention exhibit a considerably higher fungicidal activity than the compounds known from the state of the art, that is to say triphenyl-(1,2,4-triazol-1-yl)-methane and 1-(imidazol-1-yl)- and -(1,2,4-triazol-1-yl)-2-phenoxy-4,4-dimethyl-pentan-3-ols substituted in the phenyl part, which are closely related compounds chemically and from the point of view of their action. The substances according to the invention thus represent an enrichment of the art.

Particularly preferred azolyl-alkenones according to the present invention are those in which $R^1$ represents an optionally substituted phenyl or phenoxy radical, preferred substituents being halogen, straight-chain or branched alkyl with 1 to 4 carbon atoms, halogenoalkyl with 1 to 2 carbon atoms and 1 to 5 identical or different halogen atoms (such as, in particular, fluorine and chlorine atoms), and phenyl which is optionally substituted by halogen, $R^2$ represents a straight-chain or branched alkyl group with 1 to 4 carbon atoms, a cycloalkyl group with 5 to 7 carbon atoms or an optionally substituted phenyl radical, preferred possible substituents on the phenyl being those which have already been mentioned for $R^1$, and Y has the meaning indicated above.

Very particularly preferred compounds of the formula (I) are those in which $R^1$ represents a phenyl or phenoxy radical which is in each case optionally monosubstituted or polysubstituted by identical or different substituents selected from fluorine, chlorine, bromine, methyl, ethyl, phenyl and chlorophenyl, $R^2$ represents a methyl, isopropyl, tert-butyl or cyclohexyl group or a phenyl radical which is optionally monosubstituted or polysubstituted by identical or different substituents selected from fluorine, chlorine, bromine, methyl, ethyl, and phenyl, and Y has the meaning indicated above.

The following compounds of the general formula (I) may be mentioned specifically, in addition to the compounds mentioned in the preparation examples:

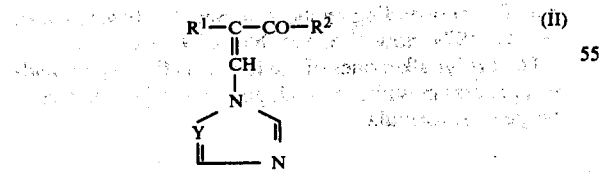

| $R^1$ | $R^2$ | Y |
|---|---|---|
| phenyl | 4-Cl-phenyl | N |
| phenyl | 2,4-diCl-phenyl | N or CH |
| 4-Cl-phenyl | phenyl | N or CH |
| 3,4-diCl-phenyl | 4-Cl-phenyl | N or CH |

-continued $$R^1-\underset{\underset{\underset{\underset{N}{\|}}{\underset{Y}{N}}}{\overset{|}{CH}}}{\overset{OH}{C}}-CH-R^2 \quad (I)$$

| $R^1$ | $R^2$ | Y |
|---|---|---|
| 2,4-Cl₂-C₆H₃- | 2-Cl-C₆H₄- | N or CH |
| 4-Cl-C₆H₄- | C₆H₅- | N or CH |
| 4-Cl-C₆H₄- | 4-Cl-C₆H₄- | N or CH |
| 4-Cl-C₆H₄- | 2,4-Cl₂-C₆H₃- | N or CH |
| C₆H₅-O- | C(CH₃)₃ | N |
| 4-Cl-C₆H₄-O- | C(CH₃)₃ | N |
| 4-CH₃-C₆H₄-O- | C(CH₃)₃ | N |
| 4-C₆H₅-C₆H₄-O- | C(CH₃)₃ | N |
| 3-Br-4-F-C₆H₃-O- | C(CH₃)₃ | N |
| 3,4-Cl₂-C₆H₃-O- | C(CH₃)₃ | N |
| 3-Cl-4-F-C₆H₃-O- | C(CH₃)₃ | N |
| C₆H₅-O- | C₆H₅ | N or CH |
| 4-Cl-C₆H₄-O- | C₆H₅ | N or CH |
| 3,4-Cl₂-C₆H₃-O- | C₆H₅ | N or CH |
| 4-F-C₆H₄-O- | C₆H₅ | N or CH |
| 4-CH₃-C₆H₄-O- | C₆H₅ | N or CH |

-continued $$R^1-\underset{\underset{\underset{\underset{N}{\|}}{\underset{Y}{N}}}{\overset{|}{CH}}}{\overset{OH}{C}}-CH-R^2 \quad (I)$$

| $R^1$ | $R^2$ | Y |
|---|---|---|
| 3-CH₃-4-Cl-C₆H₃-O- | C₆H₅ | N or CH |
| 4-C₆H₅-C₆H₄-O- | C₆H₅ | N or CH |

If for example, 1-(imidazol-1-yl)-2-(4-fluorophenoxy)-4,4-dimethyl-1-pentan-3-one and sodium borohydride are used as starting substances, the course of the reaction for the preparation of compounds of the invention is illustrated by the following equation:

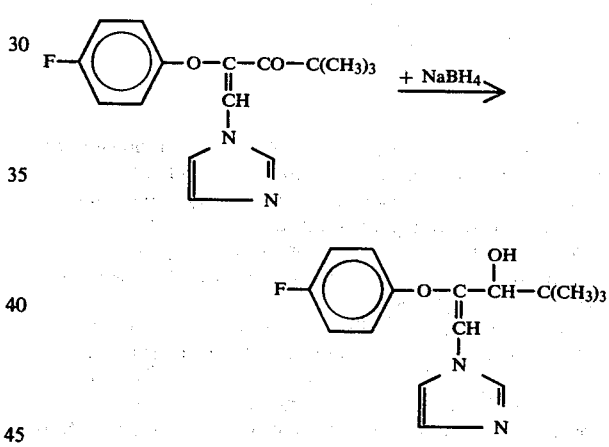

Particularly preferred azolyl-alkenones to be used as starting substances for the process according to the invention are those in which $R^1$, $R^2$ and Y represent those radicals which have already been mentioned for these substituents in the case of the preferred and particularly preferred compounds of the present invention.

The azolyl-alkenones of the formula (II) are the subject of our copending application Ser. No. 084,208, filed Oct. 12, 1979, now U.S. Pat. No. 4,291,044.

The azolyl-alkenones of the formula (II) may be made by a process in which a 1-halogeno-ethene derivative of the general formula $$R^1-\underset{\underset{\underset{Hal}{|}}{\overset{\|}{CH}}}{C}-CO-R^2 \quad (III)$$

in which $R^1$ and $R^2$ have the meaning indicated above and Hal represents a halogen atom, preferably a chlorine or bromine atom, is reacted with an alkali metal salt of an azole of the general formula

 (IV)

in which

Y has the meaning indicated above and

M represents an alkali metal, preferably sodium or potassium, in the presence of an inert organic solvent, such as acetonitrile, at temperatures between 20° and 120° C. Isolation of the compounds of the formula (II) is effected in the customary manner, it being possible to carry out a purification, if appropriate, via an acid addition salt (see also the preparative examples).

The azolyl-alkenones of the formula (II) may also be obtained by a new process according to the present invention in which a 1-halogeno-ethene derivative of the general formula

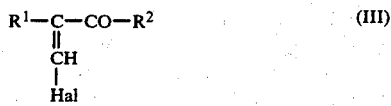 (III)

in which $R^1$, $R^2$ and Hal have the meaning indicated above, is reacted with a trimethylsilyl-azole of the general formula

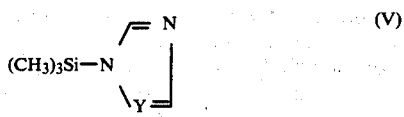 (V)

in which

Y has the meaning indicated above, in the presence of a diluent.

1-Halogeno-ethene derivatives of the formula (III) are known, and they can be obtained in a generally known manner if a corresponding ethene derivative of the general formula

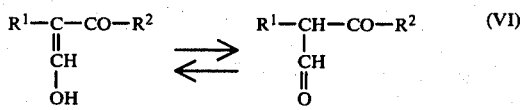 (VI)

in which $R^1$ and $R^2$ have the meaning indicated above, is reacted with a halogenating agent, such as phosphorus halides and sulphur halides, examples which may be mentioned being thionyl chloride, sulphuryl chloride, phosphorus trichloride or tribromide and phosphorus oxychloride, if appropriate in the presence of a diluent, such as, toluene or xylene, at temperatures between 20 and 100° C. (see also the preparative examples).

1-Hydroxy-ethane derivatives of the formula (VI) are known (see, inter alia, Liebigs Ann. Chem. 379, 230 (1911)), and they can be obtained in a generally known manner, by reacting a known ketone of the general formula

   $R^1$—$CH_2$—CO—$R^2$   (VII)

in which $R^1$ and $R^2$ have the meaning indicated above, with a formic acid ester of the general formula

H—CO—O—$R^3$ (VIII)

in which $R^3$ represents methyl or ethyl, in the presence of sodium methylate or ethylate in methanol or ethanol, at temperatures between 0° and 40° C. (see also the preparative examples).

The alkali metal salts of azoles of the formula (IV) are known. They are obtained by reacting imidazole or 1,2,4-triazole with sodium methylate or potassium methylate in methanol, or by reacting imidazole with an equivalent amount of the corresponding alkali metal hydride.

The trimethylsilyl-azoles of the formula (V) are likewise known (see DE-OS (German Published No.) 1,940,628). They are obtained by reacting imidazole or 1,2,4-triazole with trimethyl-chlorosilane in the presence of a base (see also Chem. Ber. 93, 2,804).

Preferred possible diluents for the new reaction of the 1-halogeno-ethene derivatives of the formula (III) with the trimethylsilyl-azoles of the formula (V) are inert, organic solvents. These include, preferably, aromatic hydrocarbons, such as benzenes or toluene; nitriles, such as acetonitrile; ketones, such as acetone; ethers, such as diethyl ether; and dimethylformamide.

The reaction temperatures can be varied within a substantial range in this reaction. In general, the reaction is carried out between about 10° C. and 120° C., preferably at the boiling point of the solvent used.

Equimolar amounts of the reactants are preferably used in carrying out this reaction. Isolation of the compounds of the formula (II) is effected in the customary manner.

The reduction according to the invention is carried out in the customary manner, for example by reaction with complex hydrides, if appropriate in the presence of a diluent, or by reaction with aluminum isopropylate in the presence of a diluent.

If complex hydrides are used, possible diluents for the reaction according to the invention are polar organic solvents. These include, preferably, alcohols, such as methanol, ethanol, butanol or isopropanol, and ethers, such as diethyl ether or tetrahydrofuran. The reaction is in general carried out at 0° to 30° C., preferably at 0° to 20° C. For this reaction, generally about 1 mol of a complex hydride, such as sodium hydride or lithium alanate, is employed per mol of the ketone of the formula (I). To isolate the reduced compounds of the formula (I), the residue is taken up in dilute hydrochloric acid and the mixture is then reduced alkaline and extracted with an organic solvent. Further working up is effected in the customary manner.

If aluminum isopropylate is used, preferred possible diluents for the reaction according to the invention are alcohols, such as isopropanol, or inert hydrocarbons, such as benzene. The reaction temperatures can again be varied within a substantial range; in general the reaction is carried out between 20° and 120° C., preferably at 50° to 100° C. To carry out the reaction, generally about 1 to 2 mols of aluminum isopropylate are employed per 1 mol of the ketone of the formula (I). To isolate the reduced compounds of the formula (I), the excess solvent is removed by distillation in vacuo and aluminum compound formed is decomposed with dilute sulphuric acid or sodium hydroxide solution. Further working up is effected in the customary manner.

All the physiologically acceptable acids can be used for the preparation of acid addition salts of the compounds of the formula (I). These acids include, as preferences, hydrogen halide acids (such as, hydrobromic acid, and in particular hydrochloric acid), phosphoric acid, nitric acid, sulphuric acid, mono-functional and bifunctional carboxylic acids and hydroxy-carboxylic acids (such as, acetic acid, maleic acid, succinic acid, fumaric acid, tartaric acid, citric acid, salicylic acid, sorbic acid and lactic acid, and sulphonic acids (such as, p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrogen chloride, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel. Possible anions of the salts are those which are derived from physiologically acceptable acids. These include, preferably, hydrogen halide acids, such as, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegative propagation stock and seeds, and of the soil.

As plant protection agents, the active compounds according to the invention can be used with particularly good success for combating those fungi which cause powdery mildew diseases, thus, for example, against the powdery mildew of cucumber causative organism (*Erysiphe cichoracearum*), the powdery mildew of apple causative organism (*Podosphaera leucotricha*) or the powdery mildew of cereal causative organism (*Erysiphe graminis*), and for combating Puccinia species, thus, for example, against the cereal rust causative organism (*Puccinia recondita*).

When applied in appropriate concentrations, the substances according to the invention also exhibit a herbicidal or growth-regulating action.

The active compounds can be converted into the customary formulations, such as solutions, emulsions, powders, suspensions, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methyl-cellulose.

Adhesives such as carboxymethylcellulose and natural and synthetic polymers in the form of powders, granules or lactices, such as gum arabic, polyvinyl alcohol and polyvinyl acetate, can be used in the formulations.

It is possible to use colorants such as inorganic pigments, for example iorn oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are generally requires at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvester crop may be improved by the present invention.

PREPARATIVE EXAMPLES

EXAMPLE 1

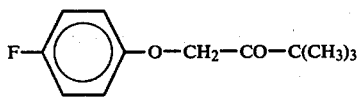
(a)

418.3 g (3.11 mols) of 2,2-dimethyl-4-chloro-butan-3-one were added dropwise to a suspension, heated to the boiling point, of 315 g (2.8 mols) of 4-fluorophenol and 386.4 g (2.8 mols) of potassium carbonate in 1,500 ml of acetone. The mixture was stirred under reflux for 4 hours. After cooling to room temperature, the salt which had separated out was filtered off and the filtrate was concentrated in vacuo. The oil which remained was distilled in vacuo. 101.5 g (86.2% of theory) of 2,2-dimethyl-4-(4-fluorophenoxy)-butan-3-one of boiling point 83°–84° C./0.05 mm Hg ($n_D^{20}=1.4919$) were obtained.

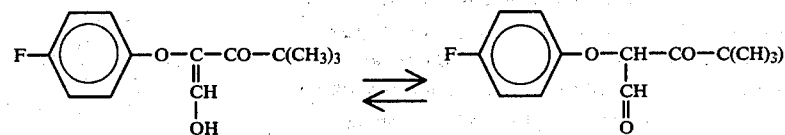
(b)

163 g (2.2 mols) of formic acid ethyl ester were added dropwise to a solution of 136 g of sodium ethylate in 1,500 ml of ethanol at 0° C. 420 g (2 mols) of 2,2-dimethyl-4-(4-fluorophenoxy)-butan-3-one were then slowly stirred in at 0° C. After a reaction time of 24 hours at 0° C., the mixture was allowed to warm to room temperature and was subsequently stirred at this temperature for a further 96 hours. The reaction mixture was poured into 5,000 ml of ice-water and the organic phase was separated off by extraction with chloroform. Unreacted starting material could be isolated from this chloroform solution and could be employed again. The aqueous phase was acidified with 10% strength hydrochloric acid, while cooling, and the oil which separated out was taken up in chloroform. The chloroform phase was dried over sodium sulphate and concentrated by distilling off the solvent in vacuo. The oil which remained was distilled in vacuo. 170 g (83% of theory, relative to reacted material) of 1-hydroxy-2-(4-fluorophenoxy)-4,4-dimethyl-1-penten-3-one of boiling point 101°–102° C./0.6 mm Hg ($n_D^{20}=1.5132$) were obtained.

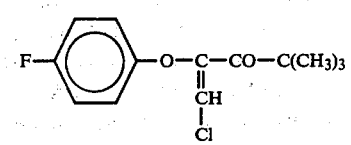
(c)

297.5 g (2.5 mols) of thionyl chloride were slowly stirred into a solution, warmed to 60° C., of 404.6 g (1.7 mols) of 1-hydroxy-2-(4-fluorophenoxy)-4,4-dimethyl-1-penten-3-one in 3,000 ml of anhydrous toluene. The mixture was kept at this temperature for 12 hours and the solvent and excess thionyl chloride were then distilled off. The oil which remained was distilled in vacuo. 353.3 g (81% of theory) of 1-chloro-2-(4-fluorophenoxy)-4,4-dimethyl-1-penten-3-one of boiling point 95°–103° C./0.3 mm Hg were obtained.

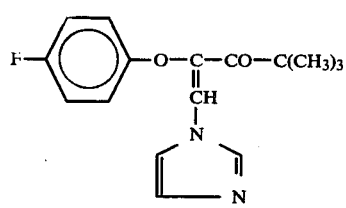

(d)

256.7 g (1 mol) of 1-chloro-2-(4-fluorophenoxy)-4,4-dimethyl-1-penten-3-one in 150 ml of acetonitrile were added dropwise to a suspension of 90 g (1 mol) of sodium imidazole, prepared from sodium methylate and imidazole in methanol, in 2,500 ml of acetonitrile, while stirring. Thereafter, the reaction mixture was heated to the boiling point for 6 hours. It was allowed to cool to room temperature and was concentrated by distilling off the solvent in vacuo. The residue was taken up in 1,000 ml of ethyl acetate, the mixture was washed three times with 200 ml of water each time and the organic phase was dried over sodium sulphate and concentrated by distilling off the solvent in vacuo. 272.4 g (94.5% of theory) of crude 1-(imidazol-1-yl)-2-(4-fluorophenoxy)-4,4-dimethyl-1-penten-3-one were obtained as a brown oil, which was purified in the customary manner, via the nitrate, and then had a refractive index of $n_D^{20} = 1.5590$.

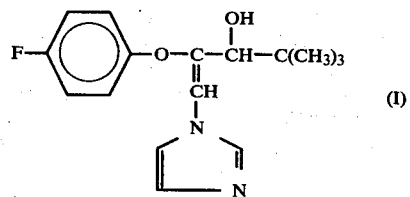

(e)

(I)

2.9 g (0.076 mol) of sodium boronate were introduced in portions into a solution of 22 g (0.076 mol) of 1-(imidazol-1-yl)-2-(4-fluorophenoxy)-4,4-dimethyl-1-penten-3-one in 200 ml of methanol at 20° to 30° C. in the course of 20 minutes, with slight external cooling and while stirring. After 3 hours, the reaction mixture was adjusted to pH 5 with 10% strength acetic acid and was then evaporated under reduced pressure.

The oily residue which remains was taken up in 250 ml of ethyl acetate and the mixture was twice extracted by shaking with 50 ml of water each time. After drying the organic phase over anhydrous sodium sulphate, the solution was evaporated in vacuo, the residue which remains was dissolved in a very little ether and petroleum ether was slowly added. The colorless crystals which separated out were filtered off, washed with a little petroleum ether and dried at 100° C. 13.7 g (62% of theory) of 1-(imidazol-1-yl)-2-(4-fluorophenoxy)-4,4-dimethyl-1-penten-3-ol of melting point 112°–113° C. were obtained.

EXAMPLE 2

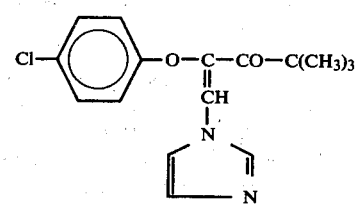

(a)

(new process variant)

13 g (0.05 mols) of 1-chloro-2-(4-chlorophenoxy)-4,4-dimethyl-1-penten-3-one and 7 g (0.05 mole) of trimethylsilylimidazole in 50 ml of toluene were heated under reflux for 5 hours. Thereafter, the reaction mixture was concentrated by distilling off the solvent in vacuo and the oily residue was separated by column chromatography (silica gel; ethyl acetate: chloroform = 1:2). 9 g (58% of theory) of 1-(imidazol-1-yl)-2-(4-chlorophenoxy)-4,4-dimethyl-1-penten-3-one of melting point 94°–95° C. were obtained.

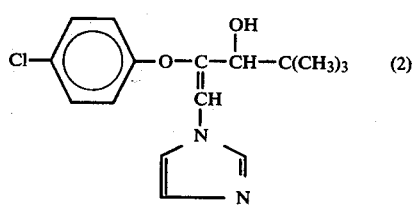

(b)

(2)

12.4 g (0.33 mols) of sodium boranate were introduced in portions into a solution of 98.8 g (0.33 mols) of 1-(imidazol-1-yl)-2-(4-chlorophenoxy)-4,4-dimethyl-1-penten-3-one in 1,000 ml of methanol at 20° to 30° C. in the course of 30 minutes, with slight external cooling. After 3 hours, the solution was filtered and the filtrate was acidified with 10% strength acetic acid and evaporated under reduced pressure. The solid residue which remained was stirred into 1.3 liters of water. The water-insoluble reduction product was filtered off and dried at 50° C. in vacuo. 93.7 g (92.55% of theory) of 1-(imidazol-1-yl)-2-(4-chlorophenoxy)-4,4-dimethyl-1-penten-3-ol of melting point 141°–143° C. were obtained in the form of colorless crystals.

The following compounds of the general formula:

$$R^1-\underset{\underset{\underset{N}{|}}{\underset{CH}{\|}}}{C}-\underset{\underset{}{|}}{\overset{OH}{\underset{}{C}H}}-R^2$$

(I)

were obtained in a manner corresponding to that indicated in Examples 1 and 2:

| Compound No. | R¹ | R² | Y | Melting Point (°C.) |
|---|---|---|---|---|
| 3 | 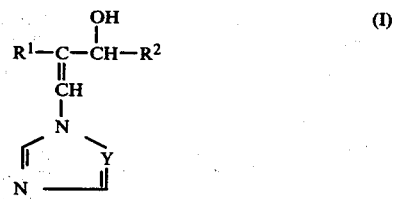 Cl—⟨○⟩—O— | C(CH₃)₃ | CH | 195–97(xHCl) |

-continued

| Compound No. | R¹ | R² | Y | Melting Point (°C) |
|---|---|---|---|---|
| 4 | C₆H₅—O— | C(CH₃)₃ | CH | 133–34 |
| 5 | 2-Cl-C₆H₄—O— | C(CH₃)₃ | CH | 103–05 |
| 6 | 2,4-Cl₂-C₆H₃—O— | C(CH₃)₃ | CH | 110–22 |
| 7 | 3-Cl-C₆H₄—O— | C(CH₃)₃ | CH | 107–08 |
| 8 | 2-Cl-4-CH₃-C₆H₃—O— | C(CH₃)₃ | CH | 137–38 |
| 9 | 2-Cl-4-F-C₆H₃—O— | C(CH₃)₃ | CH | 75–88 |
| 10 | 2-Br-4-F-C₆H₃—O— | C(CH₃)₃ | CH | 75–93 |
| 11 | 4-CH₃-C₆H₄—O— | C(CH₃)₃ | CH | 140–41 |
| 12 | 2-Cl-4-Cl-C₆H₃—O— | C(CH₃)₃ | CH | 106–08 (Decomposition) |
| 13 | 4-C₆H₅-C₆H₄—O— | C(CH₃)₃ | CH | 80–82 (Decomposition) |
| 14 | 3,4-(CH₃)₂-C₆H₃—O— | C(CH₃)₃ | CH | 110–14 |
| 15 | 2-CH₃-C₆H₄—O— | C(CH₃)₃ | CH | 92–95 |
| 16 | 2-CH₃-4-Cl-C₆H₃—O— | C(CH₃)₃ | CH | 83–85 |
| 17 | 2-Cl-4-CH₃-C₆H₃—O— | C(CH₃)₃ | N | 150–53 |
| 18 | 2,4-Cl₂-C₆H₃—O— | C(CH₃)₃ | N | 136–37 |
| 19 | 3-Cl-C₆H₄—O— | C(CH₃)₃ | N | 98–99 |
| 20 | 2-Cl-C₆H₄—O— | C(CH₃)₃ | N | 75–80 |
| 21 | 4-F-C₆H₄—O— | C(CH₃)₃ | N | 118–19 |
| 22 | 2,4-Cl₂-C₆H₃—O— | C(CH₃)₃ | N | 125–30 |
| 23 | 3,4-(CH₃)₂-C₆H₃—O— | C(CH₃)₃ | N | 118–19 |
| 24 | 2-CH₃-C₆H₄—O— | C(CH₃)₃ | N | 73–78 |
| 25 | 2-CH₃-4-Cl-C₆H₃—O— | C(CH₃)₃ | N | 117–18 |
| 26 | C₆H₅— | 4-Cl-C₆H₄— | N | 116–18 |
| 27 | 2-CH₃-4-Cl-C₆H₃—O— | C(CH₃)₃ | CH | 148–49 |
| 28 | 2-CH₃-4-Cl-C₆H₃—O— | C(CH₃)₃ | N | 108–09 |
| 29 | 2,4,6-Cl₃-C₆H₂—O— | C(CH₃)₃ | CH | 128–30 |

The fungicidal activity of the compounds of this invention is illustrated by the following examples, wherein the compounds according to the present invention are each identified by the number (given in brackets) from the preparative examples and table hereinabove.

The known comparison compounds are identified as follows:

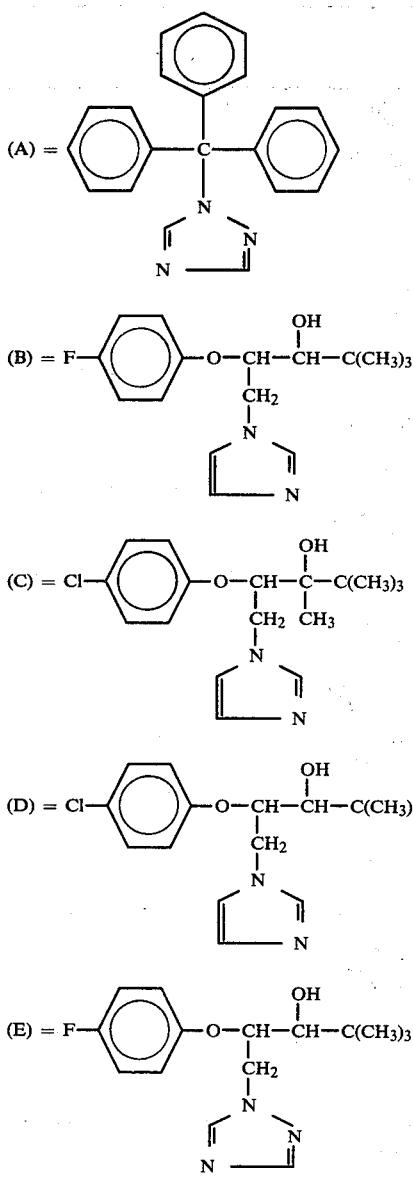

EXAMPLE 3

Shoot treatment test/powdery mildew of cereal/protective (leaf-destructive mycosis)

To produce a suitable preparation of active compound 0.25 part by weight of active compound was taken up in 25 parts by weight of dimethylformamide and 0.06 part by weight of emulsifier (alkylaryl polyglycol ether), and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis var. hordei.*

After 6 days' dwell time of the plants at a temperature of 21°–22° C. and 80–90% atmospheric humidity, the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compounds showed a very good action which was superior to that of the compound (A) known from the prior art; compounds (17), (18), (19), (20), (21), (22) and (23).

EXAMPLE 4

Shoot treatment test/cereal rust/protective (Leaf-destructive mycosis)

To produce a suitable preparation of active compound, 0.25 part by weight of active compound was taken up in 25 parts by weight of dimethylformamide and 0.06 part by weight of alkylaryl polyglycol ether emulsifier, and 975 parts by weight of water were added. The concentrate was diluted with water to the desired final concentration in the spray liquor.

To test for protective activity, single-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% atmospheric humidity.

After 100 days' dwell time of the plants at a temperature of 20° C. and 80–90% atmospheric humidity, the occurrence of rust pustules on the plants was evaluated. The degree of infection was expressed as a percentage of the infection of the untreated control plants. 0% denoted no infection and 100% denoted the same degree of infection as in the case of the untreated control. The more active the compound, the lower was the rust infection.

In this test, for example, the following compounds showed a very good action which was superior to that of the compound (B) known from the prior art: compounds (5), (6), (1), (9), (12) and (13).

EXAMPLE 5

Podosphaera test (apple)/protective

Solvent: 4.7 parts by weight of acetone
Emulsifier: 0.3 part by weight of alkylaryl polyglycol ether
Water: 95.0 parts by weight The amount of active compound required for the desired concentration of the active compound in the spray liquid was mixed with the stated amount of solvent, and the concentrate was diluted with the stated amount of water which contained the stated additions.

Young apple seedlings in the 4 to 6 leaf stage were sprayed with the spray liquid until dripping wet. The plants remained in a greenhouse for 24 hours at 20° C. and at a relative atmospheric humidity of 70%. They were then inoculated by dusting with conidia of the apple powdery mildew causative organism (*Podosphaera leucotricha*) and placed in a greenhouse at a temperature of 21° to 23° C. and at a relative atmospheric humidity of about 70%.

10 days after the inoculation, the infection of the seedlings were determined. The assessment data were converted to precent infection. 0% denoted no infection and 100% denoted that the plants were totally infected.

In this test, for example, the following compounds showed a very good action which was superior to that of the compounds (C) and (D) known from the prior art: compounds (2), (6), (7) and (20).

EXAMPLE 6

Erysiphe test (cucumbers)/protective

Solvent: 4.7 parts by weight of acetone
Emulsifier: 0.3 part by weight of alkyl-aryl polyglycol ether
Water: 95.0 parts by weight The amount of the active compound required for the desired concentration of active compound in the spray liquid was mixed with the stated amount of solvent and the concentrate was diluted with the stated amount of water which contained the stated additions.

Young cucumber plants with about three foliage leaves were sprayed with the spray liquid until dripping wet. The cucumber plants remain in a greenhouse for 24 hours to dry. They were then, for the purpose of inoculation, dusted with conidia of the fungus *Erysiphe cichoracearum*. The plants were subsequently placed in a greenhouse at 23° to 24° C. and at a relative atmospheric humidity of about 75%.

After 12 days the infection of the cucumber plants was determined. The assessment data were converted to percent infection. 0% denoted no infection and 100% denoted that the plants were totally infected.

In this test, for example, the following compounds showed a very good action which was superior to that of the compounds (C) and (D) known from the prior art: compounds (5), (6) and (9).

EXAMPLE 7

Mycelium growth test

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 parts by weight of calcium nitrate Composition of the solvent mixture:
0.19 part by weight of dimethylformamide or acetone
0.01 part by weight of alkylaryl polyglycol ether emulsifier
1.80 parts by weight of water Ratio of solvent mixture to nutrient medium:
2 parts by weight of solvent mixture
100 parts by weight of agar nutrient medium The amount of active compound required for the desired concentration of active compound in the nutrient medium was mixed with the stated amount of solvent mixture. The concentrate was thoroughly mixed, in the stated proportion, with the liquid nutrient medium, which had been cooled to 42° C., and was poured into Petri dishes of 9 cm diameter. Control plates to which the preparation had not been added were also set up.

When the nutrient medium had cooled and solidified, the plates were inoculated with the species of fungi indicated below and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. The fungus growth was rated using the following characteristic values:

1 no fungus growth;
up to 3 very strong inhibition of growth
up to 5 medium inhibition of growth
up to 7 slight inhibition of growth
9 growth equal to that of untreated control.

In this test, for example, the following compounds showed a very good action which was superior to that of the compounds (B) and (E) known from the prior art; compounds (9), (13) and (12).

The fungi used in the above procedure were

| | |
|---|---|
| *Fusarium* | *Botrytis* |
| *culmorum* | *cinerea* |
| *Sclerotinia* | *Verticillium* |
| *sclerotiorum* | *alboatrum* |
| *Fusarium* | *Pyricularia* |
| *nivale* | *oryzae* |
| *Colletotrichum* | *Phialophora* |
| *coffeanum* | *cinerescens* |
| *Rhizoctonia* | *Helminthosporium* |
| *solani* | *gramineum* |
| *Pythium* | *Mycosphaerella* |
| *ultimum* | *musicola* |
| *Cochliobolus* | *Phytophthora* |
| *miyabeanus* | *cactorum* |
| | *Pellicularia* |
| | *sasakii* |

It will be appreciated that the instant specification and examples are set forth by way of illustration and not limitation, and that various modifications and changes may be made without departing from the spirit and scope of the present invention.

What is claimed is:

1. A 1-azolyl-1-propen-3-ol of the formula

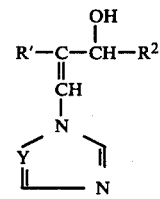

in which
R¹ is phenyl, phenoxy, or phenyl or phenoxy substituted by halogen, alkyl with 1 to 4 carbon atoms, halogenoalkyl with 1 to 2 carbon atoms and 1 to 5 halogen atoms, phenyl or halophenyl,
R² is alkyl with 1 to 4 carbon atoms, cycloalkyl with 5 to 7 carbon atoms, phenyl or phenyl substituted by halogen, alkyl with 1 to 4 carbon atoms, halogenalkyl with 1 or 2 carbon atoms and 1 to 5 halogen atoms, phenyl or halophenyl, and
Y is N or CH,
or a physiologically acceptable acid addition salt or metal salt complex thereof.

2. An acid addition salt according to claim 1 wherein the acid is a hydrogen halide acid, phosphoric acid, nitric acid, sulphuric acid, or a monofunctional or bifunctional carboxylic acid, hydroxycarboxylic or sulphonic acid, or the metal is copper, zinc, manganese, magnesium, tin, iron or nickel and the anion is chloride, bromide, phosphate, nitrate or sulphate.

3. A metal salt complex according to claim 1, wherein the metal is copper, zinc manganese, magnesium, tin, iron or nickel and the anion is chloride, bromide, phosphate, nitrate or sulphate.

4. A compound according to claim 1, wherein such compound is 1-(imidazol-1-yl)-2-(4-fluorophenoxy)-4,4-dimethyl-1-penten-3-ol of the formula

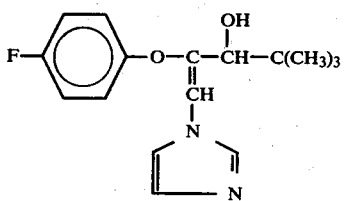

or an acid addition salt or metal salt complex thereof.

5. A compound according to claim 1, wherein such compound is 1-(imidazol-1-yl)-2-(2-chlorophenoxy)-4,4-dimethyl-1-penten-3-ol of the formula

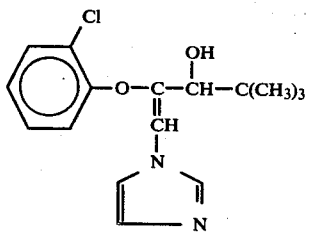

or an acid addition salt or metal salt complex thereof.

6. A compound according to claim 1, wherein such compound is 1-imidazol-1-yl)-2-(2-chloro-4-fluorophenoxy)-4,4-dimethyl-1-penten-3-ol of the formula

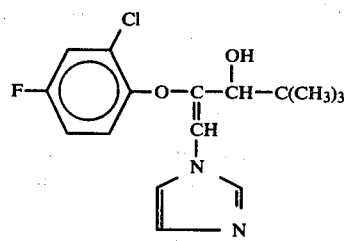

or an acid addition salt or metal salt complex thereof.

7. A compound according to claim 1, wherein such compound is 1-(1,2,4-triazol-1-yl)-2-(4-fluorophenoxy)-4,4-dimethyl-1-penten-3-ol of the formula

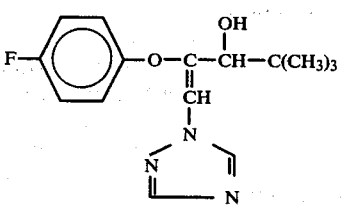

or an acid addition salt or metal salt complex thereof.

8. A fungicidal composition comprising a fungicidally effective amount of a compound, salt or complex according to claim 1 in admixture with a diluent.

9. A method of combating fungi, comprising applying to the fungi, or to a habitat thereof, a fungicidally effective amount of a compound, salt or complex according to claim 1.

10. A method according to claim 9, wherein such compound is 1-(imidazol-1-yl)-2-(4-fluorophenoxy)-4,4-dimethyl-1-penten-3-ol, 1-(imidazol-1-yl)-2-(2-chlorophenoxy)-4,4-dimethyl-1-penten-3-ol, 1-(imidazol-1-yl)-2-(2-chloro-4-fluorophenoxy)-4,4-dimethyl-1-penten-3-ol, or 1-(1,2,4-triazol-1-yl)-2-(4-fluorophenoxy)-4,4-dimethyl-1-penten-3-ol, or a salt or complex thereof.

* * * * *